US009226743B2

(12) United States Patent  (10) Patent No.: US 9,226,743 B2
Dreyfuss et al.  (45) Date of Patent: Jan. 5, 2016

(54) APPLICATOR FOR SUTURE/BUTTON CONSTRUCT WITH POSITIVE RETENTION AND CONTROL

(71) Applicant: Arthrex, Inc., Naples, FL (US)

(72) Inventors: Peter J. Dreyfuss, Naples, FL (US); Matthew T. Provencher, Coronado, CA (US)

(73) Assignee: Arthrex, Inc., Naples, FL (US)

( * ) Notice: Subject to any disclaimer, the term of this patent is extended or adjusted under 35 U.S.C. 154(b) by 387 days.

(21) Appl. No.: 13/688,445

(22) Filed: Nov. 29, 2012

(65) Prior Publication Data

US 2013/0138108 A1  May 30, 2013

Related U.S. Application Data

(60) Provisional application No. 61/564,581, filed on Nov. 29, 2011.

(51) Int. Cl.
*A61B 17/04* (2006.01)
*A61F 2/08* (2006.01)
*A61B 17/34* (2006.01)
*A61B 17/00* (2006.01)

(52) U.S. Cl.
CPC ......... *A61B 17/0401* (2013.01); *A61B 17/3468* (2013.01); *A61B 2017/00477* (2013.01); *A61B 2017/0409* (2013.01); *A61B 2017/0417* (2013.01)

(58) Field of Classification Search
CPC ........... A61B 17/0401; A61B 17/3468; A61B 2017/0404; A61B 2017/0409; A61B 2017/0414; A61B 2017/0417; A61B 2017/0419; A61B 2017/044; A61F 2/0811; A61F 2/0805; A61F 2002/0817; A61F 2/0847; A61F 2/0858; A61F 2/0864; A61F 2/087; A61F 2002/0858; A61F 2002/0864; A61F 2002/087; A61F 2002/0847
USPC .......................................................... 606/232
See application file for complete search history.

(56) References Cited

U.S. PATENT DOCUMENTS

| | | | |
|---|---|---|---|
| 6,562,044 B1 * | 5/2003 | Cooper | 606/300 |
| 8,348,960 B2 | 1/2013 | Michel et al. | |
| 2004/0199166 A1 | 10/2004 | Schmieding et al. | |
| 2004/0243178 A1 * | 12/2004 | Haut et al. | 606/232 |
| 2008/0109037 A1 * | 5/2008 | Steiner et al. | 606/232 |
| 2010/0004683 A1 * | 1/2010 | Hoof | A61B 17/0401 606/232 |
| 2011/0112576 A1 * | 5/2011 | Nguyen et al. | 606/232 |

FOREIGN PATENT DOCUMENTS

EP  1 199 035 A1  4/2002
EP  1 484 022 A2  12/2004

* cited by examiner

*Primary Examiner* — Katrina Stransky
*Assistant Examiner* — Katherine Schwiker
(74) *Attorney, Agent, or Firm* — Dickstein Shapiro LLP

(57) ABSTRACT

A technique for joint repair employing a suture/button construct and an applicator designed to securely engage a button of the suture/button construct. The button of the suture/button construct securely engages two shafts of the applicator (i.e., an angled, non-vertical flat face of the outer shaft and a threaded region of the inner shaft). Engagement to and disengagement from the applicator is conducted without rotation of the button. The applicator with the secured button is introduced into the tissue (for example, soft tissue or a bone tunnel) and the button is passed through the tissue.

22 Claims, 1 Drawing Sheet

APPLICATOR FOR SUTURE/BUTTON CONSTRUCT WITH POSITIVE RETENTION AND CONTROL

CROSS-REFERENCE TO RELATED APPLICATIONS

This application claims the benefit of U.S. Provisional Application No. 61/564,581, filed Nov. 29, 2011, the entire disclosure of which is incorporated by reference herein.

FIELD OF THE INVENTION

The present invention relates to the field of surgery and, more particularly, to an applicator for a suture/button construct in reconstructive surgeries.

BACKGROUND OF THE INVENTION

Suture/button constructs have been used for fixation of ankle syndesmosis (U.S. Pat. No. 7,235,091), acromioclavicular (AC) joint fixation (U.S. Patent Appl. Publ. No. 2007/0179531) and more recently, for small joint surgery, such as bunion repair (U.S. Pat. No. 7,875,058), or lisfranc repair (U.S. Pat. No. 7,901,431). In these small joint techniques, the suture/button construct is passed through a passage or tunnel (for example, a drilled hole) by employing a needle that pulls the button and the attached suture through the passage or tunnel. Pulling of the needle through the passage or tunnel, and subsequently out the skin, may be difficult, however, in certain circumstances, such as hallux valgus correction and lisfranc ligament repair. In addition, proper positioning of the buttons (for example, of the oblong and round button of the suture/button construct) may be difficult when the buttons are pulled through with suture and needle.

An instrument for pushing the buttons and attached suture through the drilled hole (instead of having to pull them through using the needle) is described in U.S. Patent Appl. Publ. No. 2009/0043318, the disclosure of which is incorporated in its entirety herewith. As detailed in U.S. Patent Appl. Publ. No. 2009/0043318, the shaft of the instrument is provided with an engagement mechanism that securely engages a corresponding structure (for example, a cavity or recess) of the button of the suture/button construct. The cavity (recess) of the button has a diameter about equal to the diameter of the shaft to allow a tight fit of the button to the applicator during advancement of the button through soft tissue or bone hole. The button is secured to the instrument with suture.

An instrument that would be able to push the button and attached suture through the drilled hole, and allow the button to be screwed and unscrewed from the instrument without causing rotation of the button, is needed. Also needed are methods of positive control and release of buttons used in surgical procedures, particularly in orthopedic procedures.

BRIEF SUMMARY OF THE INVENTION

The present invention provides techniques and reconstruction systems for surgical repairs. The system comprises an applicator/inserter designed for the manipulation and insertion of a fixation device (for example, a button which may be part of a suture loop/button construct) through a drilled hole or passage and then for the release of the fixation device (button), with increased control and minimal effort from the user.

The system includes an engagement/securing mechanism with at least one of (i) complementary angled (non-vertical) faces located at a most distal end of the applicator/inserter and on a side of the fixation device (button); and (ii) threads on the applicator/inserter that matingly engage threads of a recess/cavity of the fixation device (button).

The present invention also provides methods of reconstructive surgery using a fixation device (for example, a button of a suture/button construct) and an applicator/inserter assembly by inter alia: (i) securing a fixation device (button) to an applicator (inserter) by matingly engaging an angled flat end of the applicator with a an angled flat end of the fixation device (button) and/or by threading an inner shaft of the applicator to a recessed, threaded portion of the fixation device (button); and (ii) passing the fixation device (button) secured to the applicator (inserter) through the drilled tunnel or socket.

Other features and advantages of the present invention will become apparent from the following description of the invention which refers to the accompanying drawings.

DETAILED DESCRIPTION OF THE INVENTION

Figure 1:
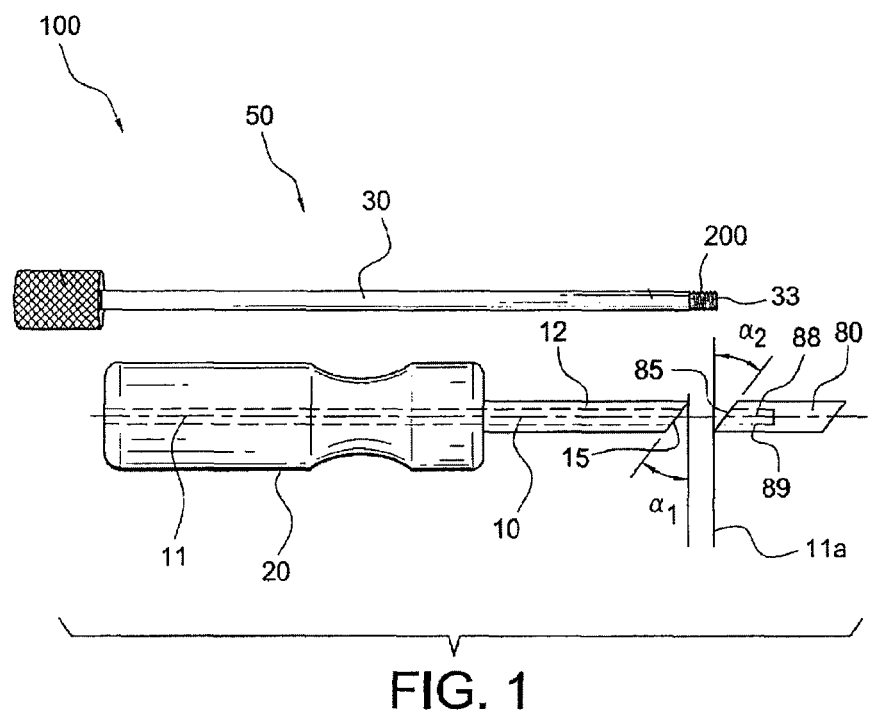
FIG. 1 illustrates the system of the present invention with the applicator/inserter and the button in the unassembled state.

The reconstruction system of the present invention comprises an applicator (inserter) designed to secure a fixation device (for example, a button), to achieve strong suture button fixation on cortical bone. The applicator is an angled and threaded device (an angled and threaded inserter) that allows secure engagement to the fixation device (button) and allows it to be uniquely controllable by a surgeon (as to having it confidently secured and then easily deployed).

The fixation device (button) is loaded onto the end of a small diameter inner shaft of the applicator by threading a most distal end of the inner shaft of the applicator into a small threaded recess on the end of the button. The outer shaft of the applicator is designed with an angled flat which mates with an angled flat on the button to allow attachment and detachment of the button to the applicator without rotation of the button. The applicator with the secured button is introduced into soft tissue or into a drilled hole in the bone, and passed through the soft tissue or bone hole.

The non-vertical, angled faces of the inserter and of the fixation device (button) provide bias to threading and unthreading of the device. When the fixation device (button) is being attached to the inserter, the angled flats on the button and on the end of the inserter keep the button from rotating during the attachment. Similarly, when the fixation device (button) is being detached from the inserter, the angled flats on the button and on the end of the inserter prevent the button from rotating during the detachment.

Prior art buttons and inserters require a surgeon to hold the sutures (attached to the button) in tension in order to keep the button on the end of the inserter. By providing threads at the most distal end of the inserter that matingly engage threads of a recess/cavity of the button, the need to hold any sutures in tension is eliminated. In addition, providing the angled face of the button that mates the angled face of the inserter confers the counterforce to unthreading such that the button could be disengaged from the inserter after being inserted into the pilot hole (thru one cortex in the humeral shaft). This allows it to be uniquely controllable by the surgeon, as to having it confidently secured and then easily deployed.

As detailed below, the reconstruction system of the present invention comprises an applicator/inserter designed for the manipulation and insertion of a fixation device (for example, a button which may be part of a suture loop/button construct) through a drilled hole or passage and then for the release of the fixation device (button), with increased control and minimal effort from the user. The system also includes an engagement/securing mechanism with at least one of (i) complementary angled faces located at a most distal end of the applicator/inserter and on a side of the fixation device (button); and (ii) threads on the applicator/inserter that matingly engage threads of a recess/cavity of the fixation device (button).

In an exemplary embodiment only, and as detailed below, the fixation device is an oblong button (of a suture/button construct, for example) and the applicator/inserter comprises a handle, an outer shaft extending from the handle, and an inner shaft housed within the handle and the outer shaft. The outer shaft is provided with a flat angled surface (non-vertical surface) at its most distal end. The inner shaft is provided with a plurality of threads at its most distal end that matingly engage threads of a recess/cavity of the button. The button is also provided with a flat angled face (non-vertical face) that mates with the corresponding flat angled face of the outer shaft. The button is held on the flat end of the applicator (and securely engaged by the applicator) by the threads of the inner shaft that matingly engage the corresponding threads of the recess/cavity of the button. The flat angled faces and the threads of the inner shaft and of the button prevent the button from rotating while it is being attached and detached from inner shaft of the applicator/inserter. The applicator with the secured button is introduced into the tissue (for example, soft tissue or a bone tunnel) and the button is passed through the tissue, and then detached at the appropriate surgical site.

Figure 2:
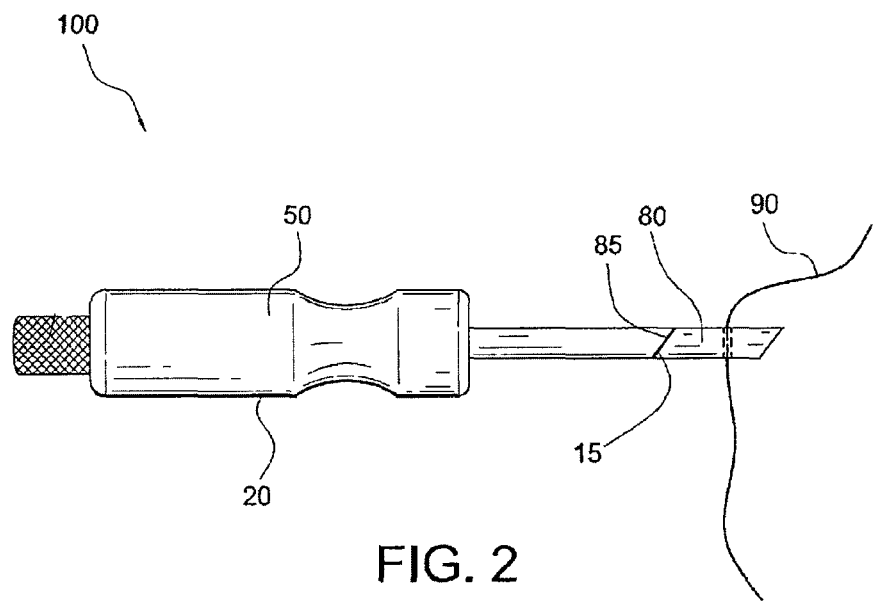
FIG. 2 illustrates the system of the present invention with the applicator/inserter and the button in the assembled state.

Referring now to the drawings, where like elements are designated by like reference numerals, FIGS. 1 and 2 illustrate assembly 100 (surgical system 100 or button/inserter assembly 100) of the present invention comprising applicator 50 that securely attaches and engages fixation device 80 through securing/engagement mechanism 200. As detailed below, the securing/engagement mechanism 200 includes at least one of the following features: (i) complementary angled, non-vertical faces located at a most distal end of the applicator/inserter 50 and on the fixation device 80; and (ii) threads on the applicator/inserter 50 that matingly engage threads of a recess/cavity of the fixation device 80. Preferably, securing/engagement mechanism 200 includes both features.

Fixation device 80 may be a button or a similar structure that allows attachment to a flexible strand and/or tissue to be fixated. In exemplary embodiments, fixation device 80 may be a button which may be part of a suture/button construct such as a suture loop/button construct, or of a construct with two buttons, for example.

Fixation device 80 may have various configurations and/or geometries as long as its body is provided with a slanted surface area (side area) and a recess/cavity extending from the slanted surface area (and as long as the body provides attachment to flexible strand(s) and/or tissue). In an exemplary embodiment only, button 80 is an oblong button (shown schematically in FIGS. 1 and 2) designed with a small hole or cavity 89 on the end of the button, to accept a threaded region of the inner shaft of the applicator 50 and to be placed at the tip of the applicator 50, as detailed below. FIG. 1 illustrates applicator 50 with button 80 in the unassembled state. FIG. 2 illustrates applicator 50 with button 80 in the assembled state, i.e., applicator 50 loaded with button 80.

Exemplary-only button 80 of FIGS. 1 and 2 has a general rectangular (oblong) configuration with both lateral sides slanted (non-vertical) and about parallel to each other. The invention is not limited to this embodiment, however, and contemplates fixation devices (buttons) with only one side slanted or with any number of sides slanted.

As shown in FIGS. 1 and 2, applicator 50 of the present invention comprises an outer shaft 10 with a longitudinal axis 11, a vertical axis 11*a*, a handle 20, and an inner rod or inner shaft 30 which is housed within the handle 20 and the outer shaft 10. The outer shaft 10 is integral with the handle 20 (forms a unitary structure). The inner rod (shaft) 30 is detachably removed from the handle 20 and outer shaft 10.

Outer shaft 10 is provided with slanted, non-vertical, angled face 15 at its most distal end 12. When assembled with button 80, the slanted, non-vertical, angled face 15 of outer shaft 10 abuts a complementary slanted, non-vertical, angled face 85 of button 80 to prevent rotation of the button as it is threadingly engaged and disengaged. For an oblong button, the angled face 85 would preferably be located on the shorter, lateral side of the button, to allow button 80 to orient longitudinally (i.e., with the longitudinal axis of the button extending about parallel to the longitudinal axis 11 of the outer shaft 10 and handle 20) for insertion within tissue (for example, a bone hole or a socket).

In an exemplary-only embodiment, the slanted, non-vertical, angled faces 15 and 85 are substantially flat, i.e., have a complementary flat profile; however, these faces may have any profile (geometry), not limited to flat surfaces, for example, may have a stepped complementary profile or any other profile as long as one surface (for example, the angled surface of the inserter) abuts and complementarily engages the corresponding complementary surface (for example, the angled surface of the button).

In an exemplary-only embodiment, the slanted, angled faces 15 and 85 are about parallel to each other and form angles α1, α2 of about 45 degree relative to vertical axis 11*a* of the applicator 50 (i.e., are non-vertical surfaces in that the most distal end surface of the applicator is slanted at an angle α1 of about 45 degrees relative to vertical axis 11*a*). However, the slanted, non-vertical, angled faces 15 and 85 may be slanted at any angles α1, α2 as long as the faces are fully complementary and abut each other. For example, angled faces 15, 85 may form an angle α1, α2 of about 30 degrees or 60 degrees relative to vertical axis 11*a* of the applicator 50.

Preferably, the surface area of the most distal slanted, angled face 15 of applicator 50 is about equal to the surface area 85 of the button 80.

Inner shaft 30 of applicator 50 is provided with an engagement mechanism 33 that is designed to securely engage a corresponding structure (for example, cavity or recess 89) of button 80. For example, and as more clearly illustrated in FIG. 1, inner shaft 30 (which is housed by shaft 10) is provided with a plurality of threads 33 designed to securely engage corresponding threads 88 formed within the recess or cavity 89 formed within the body of the button 80. The cavity or recess 89 of the button has a diameter about equal to the diameter of the threaded region 33 of smaller diameter shaft 30 to allow threading of the button and, thus, a secure engagement and fit of the button to the applicator. The cavity or recess 89 of the button communicates with the flat, angled surface 85 and extends away from the surface.

FIG. 2 illustrates assembly 100 with applicator 50 securely engaging button 80. Threads 33 of the smaller diameter shaft 30 of applicator 50 securely engage threads 88 of cavity 89 provided laterally within the body of button 80, to allow button 80 to orient longitudinally (i.e., parallel to the longitudinal axis 11 of the applicator 50) for insertion within tissue (for example, within a drilled hole or socket). In this manner, button 80 securely engages two shafts 10, 30 of the applicator 50.

A securing device may be optionally provided within or on the handle 20 of applicator 50. The securing device may comprise a rod or bolt and may be located at about the middle of the handle 20. The securing device allows a strand of flexible material 90 (for example, a suture strand 90) to wrap around it to enhance the engagement of the button 80 to the applicator shaft.

Button 80 may be part of a suture/button construct, for example, a suture loop/button construct. Button 80 is preferably formed of stainless steel, titanium alloy, titanium, PEEK or PLLA, among others. The button is provided with one or more inside eyelets that allow the passage of a flexible strand 90 such as suture. In an exemplary embodiment, the flexible strand 90 may be a single high strength suture such as Fiber-Wire® suture, sold by Arthrex, Inc. of Naples, Fla., and described in U.S. Pat. No. 6,716,234, the disclosure of which is incorporated by reference herein.

In an exemplary embodiment only, button 80 has a length of about 10 mm to about 20 mm, more preferably of about 12 mm to about 15 mm, and a width that is less than about 1 mm narrower than the width of the drill hole through which the button is inserted and subsequently passed through. Preferably, button 80 is very small, having a width that allows it to pass through a 3 mm cortical pin hole without over drilling, which in turn saves time and preserves bone.

In an exemplary embodiment, the button 80 is attached to a high strength suture, forming a suture-button assembly which may be successfully employed in various fixation techniques, for example, in AC joint fixations, soft tissue approximation or for corrections of the metatarsal angle. In these methods, the button with the attached suture is passed through a passage or tunnel (for example, a drilled hole) by pushing the button with the applicator 50 of the present invention.

The system of the present invention may be employed for fixation of bone to bone, or for fixation of soft tissue to bone. An exemplary method of reconstructive surgery using fixation device 80 (button 80) and applicator/inserter 50 comprises inter alia the steps of: (i) drilling a bone tunnel or socket; (ii) securing fixation device (button) 80 to applicator (inserter) 50 by matingly engaging an angled flat end 15 of the applicator with an angled flat end 85 of the button and/or by threading an inner shaft 30 of the applicator to a recessed, threaded portion 89 of the button 80; (iii) passing the button 80 through the drilled tunnel or socket; and (iv) detaching and securing the button 80 to the bone cortex once the button exits the tunnel or socket.

In an exemplary embodiment, assembly 100 (comprising applicator 50 and button 80) of the present invention may be used to secure a soft tissue graft in a bone socket in a retrograde manner, for example. According to another exemplary embodiment, assembly 100 of the present invention may be used to secure a bone-to-bone (BTB) graft in a femoral tunnel or socket in a retrograde manner, for example. In a particular and only exemplary embodiment, a method of reconstructive surgery using a suture/button construct and a corresponding applicator comprises, for example, the steps of: (i) forming a bone tunnel or socket in an antegrade or a retrograde manner (using a cutter which is inserted in a retrograde manner through the bone); (ii) securing a graft (soft tissue graft or BTB graft) to button 80 of a suture/button construct; (iii) securing the button 80 to applicator 50; (iv) passing the button 80 secured to the applicator 50 through the bone tunnel or socket; and (v) securing the button 80 to the bone cortex once the button 80 exits the tunnel or socket.

According to one embodiment of the present invention, the bone tunnel or socket is a femoral socket prepared by employing a retrograde drilling device provided with a cutter detachable from a guide pin, in the manner described in U.S. Patent Application Publication No. 2004/01990166, entitled "ACL Reconstruction Technique Using Retrodrill," the disclosure of which is hereby incorporated by reference herein in its entirety.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A surgical assembly, comprising:
    a fixation device comprising a body, a flat side surface, at least one eyelet extending through opposing surfaces of the body, and a threaded recess within the body of the fixation device;
    a flexible strand attached to the at least one eyelet; and
    an inserter comprising an outer shaft having a proximal end and a distal end, a handle provided at the proximal end, and an inner shaft housed within the handle, the inner shaft having a threaded distal end configured to securely engage the threaded recess of the fixation device,
    wherein a most distal end of the outer shaft of the inserter terminates in a slanted, non-vertical, angled face that matingly engages a corresponding slanted, non-vertical, angled surface on the flat side surface of the fixation device;
    wherein the threaded distal end of the inner shaft passes through the slanted, non-vertical, angled surface of the outer shaft and through the slanted, non-vertical, angled surface of the flat side of the fixation device.

2. The surgical assembly of claim 1, wherein the inner shaft extends through a whole length of the handle and through the outer shaft.

3. The surgical assembly of claim 1, wherein the fixation device is an oblong button.

4. An applicator for a suture/button construct, comprising:
    an elongated outer shaft having a longitudinal axis, a proximal end and a distal end;
    a handle provided at the proximal end; and
    an inner shaft extending through the handle and through the outer shaft, the inner shaft being provided with an engagement mechanism at a distal end configured to securely engage a button of the suture/button construct, wherein the engagement mechanism includes a plurality of threads at the most distal end of the inner shaft that engage a plurality of corresponding threads formed within a recess or cavity of the button, and
    wherein a most distal end surface of the outer shaft has a slanted, non-vertical, angled face that matingly engages a corresponding slanted, non-vertical, angled side surface of the button, wherein the angled, non-vertical face of the outer shaft is parallel to the angled, non-vertical side surface of the button;

wherein the threaded distal end of the inner shaft passes through the slanted, non-vertical, angled surface of the outer shaft and through the slanted, non-vertical, angled side surface of the button.

5. The applicator for the suture/button construct of claim 4, wherein, when the plurality of threads engage plurality of the corresponding threads formed within the recess of the button, the button is oriented coaxially with the longitudinal axis of the outer shaft.

6. The applicator for the suture/button construct of claim 4, wherein the suture/button construct comprises at least one suture strand attached to the button.

7. The applicator for the suture/button construct of claim 4, wherein the button has an oblong or round configuration.

8. A surgical system, comprising:
   a button comprising a body, a flat slanted, non-vertical angled side surface, two eyelets extending through opposing surfaces of the body, and a threaded recess provided within the body of the button and extending away from the flat slanted, non-vertical angled side surface;
   a flexible strand attached to at least one of the two eyelets; and
   a device for engaging and securing the button and for subsequently advancing the button through anatomical tissue, the device comprising two coaxial shafts;
   wherein the two coaxial shafts are an outer shaft and an inner shaft; the inner shaft comprises a distal end that is provided with a plurality of threads that securely engage the threaded recess within the body of the button;
   wherein a most distal end of the outer shaft terminates in a slanted, non-vertical, angled face that matingly engages the flat slanted, non-vertical, angled side surface of the button;
   wherein the threaded distal end of the inner shaft passes through the slanted, non-vertical, angled surface of the outer shaft and through the slanted, non-vertical, angled side surface of the button.

9. The surgical system of claim 8, wherein the device comprises an outer shaft having a proximal end, a handle provided at the proximal end, and an inner shaft extending through a whole length of the handle and of the outer shaft.

10. The surgical system of claim 9, wherein the threaded recess of the button has a diameter about equal to a diameter of the inner shaft and wherein the threaded recess extends in a direction parallel to a longitudinal axis of the device, to allow the button to be oriented coaxially with the longitudinal axis of the device when the threads of the inner shaft engage the threads of the recess within the body of the button.

11. The surgical system of claim 8, wherein the button is employed for positioning tissue attached to the button within a bone socket or tunnel.

12. The surgical system of claim 8, wherein the button is formed of a material selected from a group consisting of stainless steel, titanium, titanium alloy, polyethylene, PEEK and PLLA.

13. A method of positioning tissue within the body, comprising the steps of:
   providing a fixation device with a body, a slanted, non-vertical, angled flat side, at least one eyelet and a flexible strand attached to the at least one eyelet, and a threaded recess formed within the body of the fixation device and extending away from the slanted, non-vertical, angled flat side;
   attaching tissue to be positioned to the fixation device;
   engaging the fixation device to a threaded distal end of an inner shaft of an instrument, wherein the instrument is further provided with an outer shaft that houses the inner shaft, the outer shaft terminating in a most distal transversal and slanted, non-vertical, angled face that matingly engages the slanted, non-vertical, angled flat side of the fixation device;
   wherein the threaded distal end of the inner shaft passes through the slanted, non-vertical, angled surface of the outer shaft and through the slanted, non-vertical, angled surface of the flat side of the fixation device; and
   advancing the fixation device through a socket or tunnel in a bone.

14. The method of claim 13, wherein the step of engaging the fixation device to the threaded end of the inner shaft comprises threading the threaded end of the inner shaft to corresponding threads of the recess formed within the body of the fixation device.

15. The method of claim 13 further comprising the steps of:
   pushing the fixation device with the attached tissue through the socket or the tunnel in the bone;
   positioning the attached tissue within the socket or the tunnel in the bone; and
   securing the fixation device on a surface of the bone.

16. The method of claim 13, wherein the tissue to be positioned is biological or non-biological tissue.

17. The method of claim 13, wherein the tissue to be positioned is selected from a group consisting of ligament, tendon, bone and cartilage.

18. The method of claim 13, wherein the tissue to be positioned is soft tissue graft or BTB graft.

19. The method of claim 13, wherein the fixation device is a button.

20. A method of surgery, comprising the steps of:
   forming a bone tunnel or socket;
   providing a suture/button construct in the vicinity of the bone tunnel or socket, the suture/button construct comprising a button having a body with at least one eyelet and a continuous suture loop attached to the at least one eyelet, a flat slanted, non-vertical, angled side surface, and a threaded recess extending within the body and away from the flat slanted, non-vertical, angled side surface;
   providing an instrument in the vicinity of the suture/button construct, the instrument comprising an outer shaft having a proximal end and a distal end, a handle located at the proximal end, an inner shaft extending through a whole length of the handle and of the outer shaft, the inner shaft being provided with a most distal end that is threaded;
   securing the button to the instrument by threading the inner shaft to the threaded recess of the button, and by engaging the flat slanted, non-vertical, angled side surface of the button with a corresponding flat, slanted, non-vertical, angled surface of a most distal end of the outer shaft;
   wherein the threaded distal end of the inner shaft passes through the slanted, non-vertical, angled surface of the outer shaft and through the slanted, non-vertical, angled side surface of the button; and
   advancing the button through the bone tunnel or socket.

21. The method of claim 20, wherein the step of securing the button to the instrument is conducted without rotating the button.

22. The method of claim 20, wherein the bone tunnel or socket is formed in a retrograde manner using a rotary drill cutter.

* * * * *